US012635704B2

(12) United States Patent
Katsukawa

(10) Patent No.: US 12,635,704 B2
(45) Date of Patent: May 26, 2026

(54) METHOD FOR MANUFACTURING CHEESE-LIKE FERMENTED FOOD, AND CHEESE-LIKE FERMENTED FOOD

(71) Applicant: KIKKOMAN CORPORATION, Chiba (JP)

(72) Inventor: Masahiro Katsukawa, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 675 days.

(21) Appl. No.: 17/915,480

(22) PCT Filed: Mar. 24, 2021

(86) PCT No.: PCT/JP2021/012175
§ 371 (c)(1),
(2) Date: Sep. 29, 2022

(87) PCT Pub. No.: WO2021/200437
PCT Pub. Date: Oct. 7, 2021

(65) Prior Publication Data
US 2023/0122340 A1 Apr. 20, 2023

(30) Foreign Application Priority Data

Mar. 31, 2020 (JP) ................................. 2020-063513
Apr. 27, 2020 (JP) ................................. 2020-078315

(51) Int. Cl.
*A23C 20/02* (2025.01)
*C12N 1/14* (2026.01)
(52) U.S. Cl.
CPC .............. *A23C 20/025* (2013.01); *C12N 1/14* (2013.01)

(58) Field of Classification Search
CPC ................................ A23C 20/025; C12N 1/14
See application file for complete search history.

(56) References Cited

U.S. PATENT DOCUMENTS 4,855,148 A 8/1989 Kuribayashi et al.
5,597,594 A 1/1997 Matsuura et al.
(Continued)

FOREIGN PATENT DOCUMENTS

CA 2110415 A1 6/1994
CN 104430924 A 3/2015
(Continued)

OTHER PUBLICATIONS

"Tofu: The Hard (& Soft) Facts". Available online at https://allabout-japan.com/en/article/4087/2/ on Feb. 6, 2018. (Year: 2018).*
(Continued)

*Primary Examiner* — Erik Kashnikow
*Assistant Examiner* — Assaf Zilbering
(74) *Attorney, Agent, or Firm* — HAUPTMAN HAM, LLP

(57) ABSTRACT

A method of producing cheese-like fermented food from a soybean raw material, which has a flavor and texture similar to cheese, is provided as follows: A coagulation step S1 of coagulating a soybean raw material using at least one member selected from lactic acid bacteria, acids, and coagulants, a curd formation step S2 of separating whey from the coagulated product obtained in the coagulation step S1, thereby forming a curd, and a fermentation and aging step S3 of fermenting and aging the curd by a Koji mold are performed to produce a cheese-like fermented food containing, as an aroma component, 0.70 mg/g or more of isovaleric acid or 0.65 mg/g or more of isovaleric acid.

20 Claims, 1 Drawing Sheet

Coagulation Step ~ S1

Curd Formation Step ~ S2

Fermentation and Aging Step ~ S3

Cheese-Like Fermented Food

(56) References Cited

U.S. PATENT DOCUMENTS

| | | | |
|---|---|---|---|
| 2008/0213428 A1 | 9/2008 | Sato et al. | |
| 2010/0166912 A1 | 7/2010 | Furumai et al. | |

FOREIGN PATENT DOCUMENTS

| | | |
|---|---|---|
| JP | S5945830 A | 3/1984 |
| JP | S61166375 A | 7/1986 |
| JP | S63269946 A | 11/1988 |
| JP | H1148166 A | 6/1989 |
| JP | H494661 A | 3/1992 |
| JP | H05-000066 A | 1/1993 |
| JP | H614765 A | 1/1994 |
| JP | H06197719 A | 7/1994 |
| JP | H07031371 A | 2/1995 |
| JP | H7236417 A | 9/1995 |
| JP | H08000046 B2 | 1/1996 |
| JP | 2004129523 A | 4/2004 |
| JP | 2004141129 A | 5/2004 |
| JP | 2006180842 A | 7/2006 |
| JP | 2008154524 A | 7/2008 |
| JP | WO2006135089 A1 | 1/2009 |
| JP | 2009136158 A | 6/2009 |
| JP | 2017153458 A | 9/2017 |
| WO | 2009001443 A1 | 12/2008 |

OTHER PUBLICATIONS

"Tofu: The Hard (& Soft) Facts". Available online at https://allabout-japan.com/en/article/4087/2/. (Year: 2018).*

"Make Tofu at Home". Available online at https://www.soya.be/how-to-make-tofu.php#:~:text=Make%20tofu%20with%20dehulled%20soybeans%20First%20of,dehulled%20soybeans%20will%20have%20less%20beany%20taste. on Oct. 26, 2013 (Year: 2013).*

Matsumoto, "Adventures in Fermentation Part II: Shio-koji". Available online at https://www.nancymatsumoto.com/walkingandtalking/2013/03/adventures-in-fermentation-part-ii-shio.html#:~:text=Shio%2Dkoji%20is%20the%20miracle%20marinade%2C,and%20amylase%E2%80%94that%20act%20as%20tenderizers. on Mar. 21, 2013 (Year: 2013).*

Miki Nishiyama et al. "Preparation of a Cheese-like Food Using Soymilk, and Its Antioxidative Property and Characteristics", Nippon Shokuhin Kagaku Kogaku Kaishi, Japanese Society for Food Science and Technology, Sep. 2013, vol. 60, No. 9. 10pp.

URL:http://blog.suzuka.jp/ijushien/2016/05/20/p31402, The secret of "tofu that used whole soybeans and does not produce soybean curd refuse" [online], May 20, 2016, [retrieved on May 21, 2021], p. 1-3. 9pp.

* cited by examiner

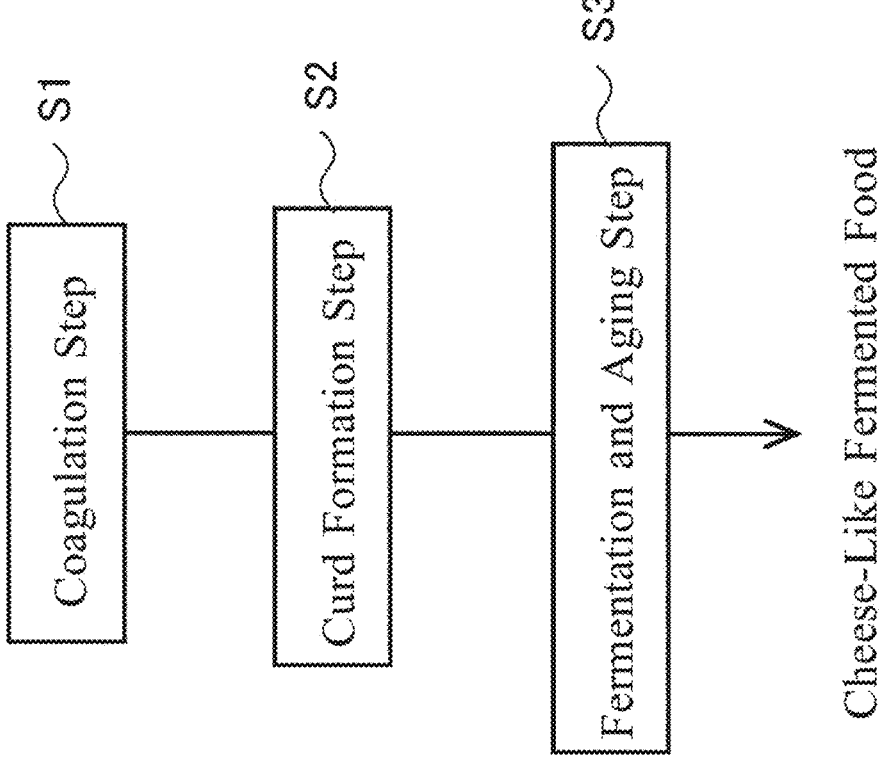

METHOD FOR MANUFACTURING CHEESE-LIKE FERMENTED FOOD, AND CHEESE-LIKE FERMENTED FOOD

RELATED APPLICATIONS

The present application is a National Phase of International Application Number PCT/JP2021/012175 filed Mar. 24, 2021 and claims priority to Japanese Application Numbers 2020-063513 filed Mar. 31, 2020 and 2020-078315 filed Apr. 27, 2020.

TECHNICAL FIELD

The present invention relates to a technique for manufacturing a cheese-like fermented food from a soybean raw material.

BACKGROUND ART

Conventionally, various studies have been made on techniques for manufacturing cheese-like fermented foods from soybean raw materials such as soymilk (see, e.g., Patent Literatures 1 to 4 and Non Patent Literature 1). Patent Literature 1 proposes a method for manufacturing a cheese-like food, wherein soymilk, from which 60% or more of the soluble sugar fraction in the raw material soybeans has been removed, is fermented and aged in the same manner as for cheese. In addition, in Non Patent Literature 1, with respect to soymilk cheeses prepared changing the kind of lactic acid bacteria used for lactic acid fermentation and the kind of cheese molds used for fermentation and aging, the component analysis results and the antioxidative property evaluation results are disclosed.

However, by simply replacing the raw material from milk with soymilk as in the methods described in Patent Literature 1 and Non Patent Literature 1, the smell and taste peculiar to soymilk are strong, and a fermented food having a flavor similar to cheese cannot be obtained. Thus, Patent Literature 2 proposes, in order to reduce the taste and smell peculiar to soybeans, a method for manufacturing cheese-like soybean fermented food, in which lactic acid bacteria derived from plant substances selected from *Lactococcus lactis* subspecies *lactis* Cu-1 strain or/and *Lactobacillus plantarum* AP-1 strain are added to a soybean raw material to perform lactic acid fermentation, and the resulting fermented product is solidified into a solid form and aged.

In addition, Patent Literature 3 proposes, in order to obtain a processed cheese-like food without use of special soymilk or long-term aging through mold application, a method for manufacturing a cheese-like food by warming and filtering a curd obtained by fermenting soymilk with lactic acid bacteria having protease activity. Further, Patent Literature 4 proposes, in order to obtain a natural cheese-like fermented food that is excellent in digestibility and also has a good flavor in terms of aroma and taste, and composition, a method in which a curd processed in the usual manner of a cheese production method is placed in a mold and pressed into a solid form, and then, while blocking contact with air, fermented and aged in a brewed product that uses Koji as a substrate.

Meanwhile, in order to enhance the nutritional value, a method for manufacturing a fermented food using soy flour containing okara (soy pulp) instead of soymilk has also been proposed (see Patent Literature 5). For example, in the method for manufacturing a lactic acid bacteria fermented product described in Patent Literature 5, soy flour obtained by crushing whole soybeans heat-treated in two steps is dispersed and dissolved in hot water to give a soy flour dispersion solution, and the soy flour dispersion solution is homogenized by a protease treatment and then fermented with lactic acid bacteria.

CITATION LIST

Patent Literatures

Patent Literature 1: JP H7-236417 A
Patent Literature 2: JP 2009-136158 A
Patent Literature 3: WO 2009/001443
Patent Literature 4: JP S63-269946 A
Patent Literature 5: JP 2017-153458 A

Non Patent Literatures

Non Patent Literature 1: Miki Nishiyama, 5 others, "Preparation of a Cheese-like Food Using Soymilk, and Its Antioxidative Property and Characteristics", Nippon Shokuhin Kagaku Kogaku Kaishi, Japanese Society for Food Science and Technology, September 2013, Vol. 60, No. 9

SUMMARY OF INVENTION

Technical Problem

However, with the conventional methods described above, it is difficult to manufacture a fermented food that has a flavor and texture similar to cheese using a soybean raw material such as soymilk or okara. Specifically, even when lactic acid bacteria derived from plant substances are added during lactic acid fermentation as in the method described in Patent Literature 2, the aroma component or umami (fifth category of taste, corresponding to the teste of glutamates, succinate or Inosinate etc.) component peculiar to cheese is not generated. In addition, in the case where only lactic acid fermentation is performed, and no aging step is performed during the manufacture as in the methods described in Patent Literatures 3 and 5, the aroma component peculiar to cheese is not generated, and, as a result, a flavor similar to cheese cannot be obtained.

Meanwhile, according to the method described in Patent Literature 4, fermentation and aging are performed in a brewed product that uses Koji as a substrate, and thus the taste and flavor greatly vary depending on the brewed product used. Therefore, it is difficult to obtain a natural flavor similar to cheese. In addition, the method described in Patent Literature 4 also has a problem in that when a brewed product that uses yeast-added Koji as a substrate is used, alcohol is generated, or sugar is consumed by the yeast, which changes the flavor.

Thus, an object of the present invention is to manufacture a cheese-like fermented food that has a flavor and texture similar to cheese from a soybean raw material such as soymilk or okara.

Solution to Problem

The method for manufacturing a cheese-like fermented food according to the present invention includes: a coagulation step of coagulating a soybean raw material using at least one member selected from lactic acid bacteria, acids, and coagulants; a step of separating whey from the coagulated product obtained in the coagulation step, thereby forming a curd; and a step of fermenting and aging the curd with a Koji.

As the soybean raw material, for example, soymilk manufactured using dehulled soybeans can be used.

Alternatively, the soybean raw material may also contain soymilk and okara. In such a case, the dry mass of the okara is 50 mass % or less (excluding 0 mass %) of the total mass.

At this time, it is possible that a blend of 2.5 to 38.3 parts by mass, on a dry mass basis, of okara with 100 parts by mass of soymilk is used as the soybean raw material. In addition, it is also possible that either or both of the soymilk and the okara is manufactured using dehulled soybeans.

Further, as the okara, an okara powder can also be used.

In such a method for manufacturing a cheese-like fermented food, in the fermentation and aging step, a Koji mold for soy sauce and/or a Koji mold for miso can be used as the Koji mold. Specifically, *Aspergillus oryzae* and/or *Aspergillus sojae* can be used.

In such a case, in the fermentation and aging step, a liquid containing spores of koji mold can be sprayed to the surface of the curd, or the curd can be mixed with spores of koji mold, soybean Koji (soybeans fermented by a bean-fermenting koji mold), or rice Koji (rice fermented by a rice-fermenting koji mold).

The fermented food according to the present invention is obtainable by fermenting and aging, with a Koji mold, a curd formed from a coagulated product of a soybean raw material, and is configured such that 0.70 mg/g or more of isovaleric acid is contained as an aroma component.

Another fermented food according to the present invention is obtainable by fermenting and aging, with a Koji mold, a curd formed from a coagulated product of a raw material containing soymilk and okara, and is configured such that the okara content (dry mass) in the raw material is 50 mass % or less (excluding 0 mass %) of the total mass, and 0.65 mg/g or more of isovaleric acid is contained as an aroma component.

Here, "soybean raw material" in the present invention means a material directly obtained from soybeans, and, for example, soymilk, soy flour, soy slurry, okara, soy protein, and the like can be mentioned.

Advantageous Effects of Invention

According to the present invention, using a soybean raw material such as soymilk or okara, a cheese-like fermented food that has a flavor and texture more similar to cheese than conventional soymilk fermented foods can be obtained.

BRIEF DESCRIPTION OF DRAWINGS

FIG. 1 is a flowchart showing the production process for a cheese-like fermented food of an embodiment of the present invention.

DESCRIPTION OF EMBODIMENTS

Hereinafter, embodiments for carrying out the present invention will be described in detail with reference to the accompanying drawings. Incidentally, the present invention is not limited to the embodiments described below.

First Embodiment

FIG. 1 is a flowchart showing the production process for a cheese-like fermented food according to an embodiment of the present invention. As shown in FIG. 1, in the method for producing a cheese-like fermented food of this embodiment, a coagulation step (step S1), a curd formation step (step S2), and a fermentation and aging step (step S3) are performed.

[Coagulation Step]

In the coagulation step S1, a soybean raw material is coagulated using at least one member selected from lactic acid bacteria, acids, and coagulants to give a coagulated product. The soybean raw material used in the method for producing a cheese-like fermented food of this embodiment may be any material directly obtained from soybeans, and, for example, soymilk, soy flour, soy slurry, okara, soy protein, and the like can be mentioned. Among them, soymilk is particularly preferable. Soymilk is not particularly limited as long as it is obtained by grinding water-soaked, hydrated soybeans and filtering insoluble components such as okara, but soymilk produced using dehulled soybeans is preferable. When soymilk produced using dehulled soybeans is used as the soybean raw material, the grassy smell peculiar to soybeans is reduced, and a fermented food having a flavor more similar to cheese can be obtained.

Incidentally, the soybean raw material used as a raw material is not limited to one kind, and it is also possible to use a combination of several kinds different in the kind of soybeans or the processing method. The soybean raw material may be subjected to a sterilization treatment before the addition of lactic acid bacteria or the like, or it is also possible to use a sterilization-treated material. Further, in the case of coagulation by lactic acid fermentation, sugar may be added to the soybean raw material, if necessary.

Then, in the case where the soybean raw material is coagulated using lactic acid, lactic acid bacteria are added to the soybean raw material to perform lactic acid fermentation. As the lactic acid bacteria used at this time, for example, lactic acid bacteria of the genus *Streptococcus* such as *Streptococcus thermophilus*, lactic acid bacteria of the genus *Lactobacillus* such as *Lactobacillus bulgaricus, Lactobacillus casei, Lactobacillus acidophilus, Lactobacillus gasseri*, and *Lactobacillus delbrueckii*, lactic acid bacteria of the genus *Lactococcus* such as *Lactococcus lactis*, lactic acid bacteria of the genus *Leuconostoc* such as *Leuconostoc mesenteroides* and *Leuconostoc lactis*, lactic acid bacteria of the genus *Enterococcus* such as *Enterococcus faecalis* and *Enterococcus faecium*, lactic acid bacteria of the genus *Bifidobacterium* such as *Bifidobacterium bifidum* and *Bifidobacterium adolescentis*, and lactic acid bacteria of the genus *Pediococcus* such as *Pediococcus pentosaceus* and *Pediococcus halophilus* can be mentioned. However, examples are not limited thereto as long as the soybean raw material can be aggregated.

The conditions for lactic acid fermentation are not particularly limited and can be suitably set according to the kind of soybean raw material or lactic acid bacteria. For example, in the case of fermentation with the lactic acid bacteria described above, fermentation may be performed under a temperature condition of 20 to 43° C. for about 4 to 20 hours. As a result, the soybean raw material is coagulated, and a coagulated product having a pH of 5 or less is obtained. Incidentally, the coagulated product obtained by lactic acid fermentation is preferably heated and sterilized at a temperature that makes the center temperature 85° C. or more for about 1 to 15 minutes for the purpose of sterilizing the lactic acid bacteria and promoting whey discharge.

Meanwhile, in the case where the soybean raw material is coagulated with an acid, an organic acid, such as citric acid, lactic acid, acetic acid, ascorbic acid, or gluconic acid, or an inorganic acid, such as dilute hydrochloric acid, is added to the soybean raw material to adjust the pH of the soybean raw material to be acidic. In addition, in the case where the soybean raw material is coagulated with a coagulant, a divalent metal salt used as a coagulant for tofu, such as magnesium chloride or calcium chloride, may be added to the soybean raw material.

[Curd Formation Step]

In the curd formation step S2, whey is separated from the coagulated product obtained in the coagulation step S1, thereby forming a curd. As the method for separating whey, methods used in the production of cheese can be applied. For example, the coagulated product is wrapped in a cotton cloth, or placed in a mold or hoop, and allowed to stand under a predetermined pressure overnight. As a result, whey is discharged, and a curd having moderate hardness is obtained.

Incidentally, in the case where salt is added to the cheese-like fermented food, for example, it is possible that the curd obtained by discharging whey is broken once, followed by adding salt, then again wrapped in a cotton cloth, or placed in a mold or hoop, and allowed to stand under a predetermined pressure for 4 to 12 hours, thereby reshaping the curd. Alternatively, for example, the curd can also be salted by immersion in a 20% saline solution for 10 minutes to overnight.

[Fermentation and Aging Step]

In the fermentation and aging step S3, a Koji mold is attached to the curd formed in the whey separation step, and the card is fermented and aged with this Koji mold. The kind of Koji mold is not particularly limited, but a Koji mold for soy sauce and a Koji mold for miso are preferable, and it is more preferable to use *Aspergillus oryzae, Aspergillus sojae*, or both of them. As a result, a cheese-like fermented food that exhibits a flavor similar to cheese and also has a smooth texture together with umami can be obtained. Incidentally, the Koji mold may be used alone, but it is also possible to use a combination of two or more kinds.

The method for attaching a Koji mold is not particularly limited either. For example, a method in which, in such a manner that a Koji mold is attached to the entire surface of the curd, a liquid containing spores of koji mold is sprayed to the curd, or spores of koji mold, soybean Koji, or rice Koji of the Koji mold is mixed with the curd, for example, can be applied.

The aging period can be suitably set according to the kind of cheese-like fermented food to be produced and the aging temperature. For example, in the case where a fermented food with a fresh aroma and a sour, light flavor like cottage cheese or cream cheese is produced, the aging period is preferably short. Meanwhile, in the case where a fermented food with strong umami and a mellow flavor like Parmi-giano-Reggiano is produced, aging for one month or longer is preferable. Incidentally, the cheese-like fermented food of this embodiment is provided with a cheese-like flavor and texture as a result of being aged at a constant temperature and humidity (mainly at a low temperature of 7 to 16° C.).

Industrially, the Koji mold-attached curd is allowed to stand, for example, under a temperature condition of 25 to 35° C. for 1 to 4 days to grow the Koji mold, and then allowed to stand, for example, under a temperature condition of 15 to 25° C. for 10 to 60 days to be aged, thereby giving a cheese-like fermented food. At this time, the curd on which the Koji mold has grown may be hermetically sealed and packaged in a film bag containing an oxygen scavenger, or wrapped in a paraffin paper, and aged in that state. As a result, the growth of the Koji mold stops, whereby the generation of an unpleasant smell caused by the active growth of a Koji mold is prevented. At the same time, contamination with harmful microorganisms and their multiplication are suppressed, and fermentation and aging with an enzyme produced by the Koji mold can be performed in such a state.

The cheese-like fermented food produced by the method described above contains 0.70 mg/g or more of isovaleric acid as an aroma component and exhibits a flavor and texture more similar to cheese than conventional products produced using soybean raw materials. In the case where the amount of isovaleric acid in the fermented food is less than 0.70 mg/g, a flavor similar to cheese cannot be obtained. Incidentally, the isovaleric acid content herein is a value measured using gas chromatography.

As described above in detail, in the method for producing a cheese-like fermented food of this embodiment, a curd formed from a soybean raw material is fermented and aged with a Koji mold. Therefore, as compared to conventional soymilk fermented foods produced using cheese molds, the grassy smell peculiar to soymilk is suppressed, and a fermented food having a flavor more similar to cheese can be obtained. The cheese-like fermented food produced by the method of this embodiment has a smooth texture, and umami can also be noted.

Second Embodiment

Next, a method for producing a cheese-like fermented food according to a second embodiment of the present invention will be described. Also in the method for producing a cheese-like fermented food of this embodiment, as in the first embodiment described above, the coagulation step (step S1), curd formation step (step S2), and fermentation and aging step (step S3) shown in FIG. 1 are performed.

[Coagulation Step]

In the coagulation step S1, a raw material containing soymilk and okara, wherein the okara content (dry mass) is 50 mass % or less (excluding 0 mass %) of the total mass, is coagulated using at least one member selected from lactic acid bacteria, acids, and coagulants, thereby giving a coagulated product. Soymilk used for the raw material may be soymilk obtained by separating insoluble components, such as okara, from a soybean juice obtained by grinding water-soaked, hydrated soybeans.

In addition, as okara used for the raw material, okara generated in the course of tofu or soymilk production can be used. Among various kinds of okara, it is preferable to use soymilk okara generated in the course of soymilk production. Soymilk okara can be obtained, for example, by centrifugation from a soybean juice obtained by crushing water-soaked soybeans. In addition, in the method for producing a cheese-like fermented food of this embodiment, although raw okara may be used, it is preferable to use an okara powder obtained by drying and powdering raw okara, and a soymilk okara powder is particularly preferable.

As okara, from the viewpoint of eliminating the roughness of the resulting coagulated product, and improving the texture, it is preferable to use fine particles. Specifically, its particle size (median size) measured by particle size analysis using a laser diffraction particle size distribution analyzer, a laser diffraction/scattering method (ISO13320, ISO9276, JIS Z8825: 2013), is preferably 500 μm or less, more preferably 200 μm or less, and still more preferably 100 μm or less.

The kinds of soymilk and okara used for the raw material are not particularly limited, but it is preferable to use soymilk or okara produced using dehulled soybeans. As a result, the grassy smell peculiar to soybeans is reduced, and a fermented food having a flavor more similar to cheese can be obtained. Incidentally, the soymilk or okara used for the raw material is not limited to one kind, and it is also possible to use a combination of several kinds different in the kind of soybeans or the processing method.

However, when the amount of okara in the raw material is more than 50 mass % on a dry mass basis, the dry and crumbly texture derived from okara stands out, and the roughness remains even after the fermentation and aging step, making it impossible to obtain a smooth texture. Thus, in the raw material used in the method for producing a cheese-like fermented food of this embodiment, the amount of okara based on the total mass is specified to be 50 mass % or less (excluding 0 mass %) on a dry mass basis. Incidentally, although the rest of components other than okara in the raw material is mainly soymilk, as long as the advantageous effects of the present invention are not impaired, components other than soymilk and okara, such as various seasonings, aromatic vegetables, herbs, and pigments, may also be contained.

In addition, the blending ratio between soymilk and okara in the raw material is not particularly limited, but it is preferable that 2.5 to 38.3 parts by mass, on a dry mass basis, of okara is blended with 100 parts by mass of soymilk. By blending soymilk and okara in the above ratio, the dietary fiber content in the fermented food can be increased without impairing the cheese-like flavor.

From the comparison between Dietary Reference Intakes for Japanese, 2020 (Ministry of Health, Labour and Welfare) and the results of National Health and Nutrition Examination Survey, 2018 (Ministry of Health, Labour and Welfare), it can be seen that men and women between the ages of 20 and 59, who are especially deficient in dietary fiber, are deficient in dietary fiber by 4.0 to 8.1 g. Thus, by ingesting 100 g of a cheese-like fermented food produced by blending 2.5 parts by mass, on a dry mass basis, of okara with 100 parts by mass of soymilk, the lack of dietary fiber described above can be offset.

The raw material may be subjected to a sterilization treatment after mixing soymilk and okara, or it is also possible to use soymilk or okara that has been sterilization-treated. Further, water or sugar can also be added to the raw material, if necessary.

In the method for producing a cheese-like fermented food of this embodiment, in the case where the raw material is coagulated using lactic acid, lactic acid bacteria are added to the raw material containing soymilk and okara to perform lactic acid fermentation. As the lactic acid bacteria used at this time, for example, lactic acid bacteria of the genus *Streptococcus* such as *Streptococcus thermophilus*, lactic acid bacteria of the genus *Lactobacillus* such as *Lactobacillus bulgaricus, Lactobacillus casei, Lactobacillus acidophilus, Lactobacillus gasseri*, and *Lactobacillus delbrueckii*, lactic acid bacteria of the genus *Lactococcus* such as *Lactococcus lactis*, lactic acid bacteria of the genus *Leuconostoc* such as *Leuconostoc mesenteroides* and *Leuconostoc lactis*, lactic acid bacteria of the genus *Enterococcus* such as *Enterococcus faecalis* and *Enterococcus faecium*, lactic acid bacteria of the genus *Bifidobacterium* such as *Bifidobacterium bifidum* and *Bifidobacterium adolescentis*, and lactic acid bacteria of the genus *Pediococcus* such as *Pediococcus pentosaceus* and *Pediococcus halophilus* can be mentioned. However, examples are not limited thereto as long as the raw material containing soymilk and okara can be aggregated.

The conditions for lactic acid fermentation are not particularly limited and can be suitably set according to the kind of raw material or lactic acid bacteria. For example, in the case of using the lactic acid bacteria described above, fermentation may be performed under a temperature condition of 20 to 43° C. for about 4 to 20 hours. As a result, protein in the raw material coagulates, and a lactic acid fermented product having a pH of 5 or less is obtained. Incidentally, the coagulated product obtained by lactic acid fermentation is preferably heated and sterilized at a temperature that makes the center temperature 85° C. or more for about 1 to 15 minutes for the purpose of sterilizing the lactic acid bacteria and promoting whey discharge.

Meanwhile, in the case where the raw material is coagulated with an acid, an organic acid, such as citric acid, lactic acid, acetic acid, ascorbic acid, or gluconic acid, or an inorganic acid, such as dilute hydrochloric acid, is added to the raw material to adjust the pH to be acidic. In addition, in the case where the raw material is coagulated with a coagulant, a divalent metal salt used as a coagulant for tofu, such as magnesium chloride or calcium chloride, may be added to the raw material.

[Curd Formation Step]

In the curd formation step S2, whey is separated from the coagulated product, thereby forming a curd. As the method for separating whey, methods used in the production of cheese can be applied. For example, the coagulated product is wrapped in a cotton cloth, or placed in a mold or hoop, and allowed to stand under a predetermined pressure overnight. As a result, whey is discharged, and a curd having moderate hardness is obtained.

Incidentally, in the case where salt is added to the cheese-like fermented food, for example, it is possible that the curd obtained by discharging whey is broken once, followed by adding salt, then again wrapped in a cotton cloth, or placed in a mold or hoop, and allowed to stand under a predetermined pressure for 4 to 12 hours, thereby reshaping the curd. Alternatively, for example, the curd can also be salted by immersion in a 20% saline solution for 10 minutes to overnight.

[Fermentation and Aging Step]

In the fermentation and aging step S3, a Koji mold is attached to the curd formed in the curd formation step S2, and the curd is fermented and aged with this Koji mold. The kind of Koji mold is not particularly limited, but a Koji mold for soy sauce and a Koji mold for miso are preferable, and it is more preferable to use *Aspergillus oryzae, Aspergillus sojae*, or both of them. As a result, a cheese-like fermented food that exhibits a flavor similar to cheese and also has a smooth texture together with umami can be obtained. Incidentally, the Koji mold may be used alone, but it is also possible to use a combination of two or more kinds.

The method for attaching a Koji mold is not particularly limited either. For example, a method in which, in such a manner that a Koji mold is attached to the entire surface of the curd, a liquid containing spores of koji mold is sprayed to the curd, or spores of koji mold, soybean Koji, or rice Koji of the Koji mold is mixed with the curd, for example, can be applied.

Meanwhile, the aging period can be suitably set according to the kind of cheese-like fermented food to be produced and the aging temperature. For example, in the case where a fermented food with a fresh aroma and a sour, light flavor like cottage cheese or cream cheese is produced, the aging period is preferably short. Meanwhile, in the case where a fermented food with strong umami and a mellow flavor like Parmigiano Reggiano is produced, aging for one month or longer is preferable. Incidentally, the cheese-like fermented food of this embodiment is provided with a cheese-like flavor and texture as a result of being aged at a constant temperature and humidity (mainly at a low temperature of 7 to 16° C.).

Industrially, the Koji mold-attached curd is allowed to stand, for example, under a temperature condition of 25 to 35° C. for 1 to 3 days to grow the Koji mold, and then allowed to stand, for example, under a temperature condition of 15 to 25° C. for 10 to 60 days to be aged, whereby a cheese-like fermented food can be obtained. At this time, by changing the aging conditions, different kinds of cheese-like fermented foods can be produced. For example, when the Koji mold is actively grown, a cheese-like fermented food with a strong Koji smell like blue cheese can be made.

In addition, in order to make cheese with a less Koji smell, for example, the curd on which a Koji mold has grown may be hermetically sealed and packaged in a film bag containing an oxygen scavenger, or wrapped in a paraffin paper, and aged in that state. As a result, the growth of the Koji mold stops, and a cheese-like fermented food, in which the generation of a Koji smell caused by the active growth of a Koji mold is suppressed, can be produced. Further, it is preferable that the curd is fermented while suppressing contamination with harmful microorganisms and their multiplication. As a result, cheese-like fermentation and aging with an enzyme produced by the Koji mold during the aging period can be performed.

The cheese-like fermented food produced by the method described above contains 0.65 mg/g or more of isovaleric acid as an aroma component. The isovaleric acid content herein is a value measured using gas chromatography. Isovaleric acid brings a flavor similar to cheese. Although the fermented food produced by the method of this embodiment is produced using soymilk and okara, its isovaleric acid content is high, and thus a flavor similar to cheese is exhibited.

As described above in detail, the method for producing a cheese-like fermented food of this embodiment performs fermentation and aging with a Koji mold. Therefore, even when okara is contained in the raw material, the grassy smell peculiar to soymilk is suppressed, and a cheese-like fermented food that exhibits a smooth texture without roughness can be obtained. In addition, because soymilk and okara are used in the raw material, the cheese-like fermented food of this embodiment has a high nutritional value, and umami can also be noted.

EXAMPLE

Hereinafter, advantageous effects of the present invention will be specifically described with reference to examples and comparative examples.

First Example

In this example, cheese-like fermented foods were produced by the following method changing only the aging period. The umami, flavor, and texture were evaluated, and also the aroma component was analyzed.

As a soybean raw material, plain soymilk manufactured by Kikkoman Beverage Co., Ltd., heat-sterilized at a center temperature of 85° C. or more for 15 minutes was used. To the sterilized soybean raw material, lactic acid bacteria (*Streptococcus thermophilus, Lactobacillus delbrueckii* subsp. *bulgaricus,* and *Lactobacillus helveticus*) were added, and lactic acid fermentation was performed at a fermentation temperature of 43° C. for 4.5 to 7 hours. The fermented soymilk obtained by such lactic acid fermentation was heat-sterilized at a center temperature of 85° C. or more for 1 minute, then wrapped in a cotton cloth and a mold, and allowed to stand under pressure overnight to discharge whey, thereby forming a curd.

Next, the formed curd was broken once, and salt in amount of 4 mass % based on the total mass of the curd was added. The curd was then wrapped in a cotton cloth and a mold and allowed to stand under pressure for 5 hours, thereby reshaping the curd. Then, to the entire surface of the obtained curd, spores of koji mold (*Aspergillus oryzae*: Yoi Tane Koji for Shoyu, manufactured by Bio'c Co., Ltd.) was sprayed. At this time, a suspension of 0.103 g of spores of koji mold in 10 ml of a 0.9 mass % saline solution was used.

The Koji mold-attached curd was allowed to stand under a temperature condition of 25° C. for 2 or 3 days to grow the Koji mold until the surface became yellow and slightly green. Then, each sample was placed in a film bag containing an oxygen scavenger, hermetically sealed, and allowed to stand under a temperature condition of 15° C. for a predetermined period to be aged.

<Sensory Evaluation>

Each sample after aging was taken out from the bag and subjected to sensory evaluation by two panelists for umami, texture (smoothness), and flavor. As a result, with respect to the taste, ◯ was given when the two panelists both noted umami, Δ was given when one of them noted umami, and × was given when none of them noted umami. Also with respect to the flavor, ◯ was given when the two panelists both noted a flavor similar to cheese, Δ was given when one of them noted a flavor similar to cheese, and × was given when none of them noted a flavor similar to cheese. With respect to the texture, ◯ was given when the two panelists both noted smoothness (no roughness), Δ was given when only one of them noted smoothness, and × was given when they both noted roughness.

<Aroma Component Analysis>

The aroma component was analyzed by gas chromatography (HERACLES II, manufactured by Alpha Moss Japan), and the concentration of isovaleric acid, which is the aroma component peculiar to cheese, was calculated. At this time, 2 g of a sample was enclosed in a 20-ml vial, and the components inside the vial were concentrated and extracted by SPME (solid-phase microextraction method). The trap temperature was set at 40° C./240° C. (desorption temperature), and hydrogen was used as the carrier gas. A metal capillary column (MXT-5/MXT-WAX) was used as the column, and the column temperature rise conditions were such that the initial temperature was 40° C., the initial isothermal time was 10 seconds, and the temperature was raised from 40° C. to 250° C. at a temperature rise rate of 1.5° C./sec. Detection was performed at an FID temperature of 260° C.

The results of the above are shown in Table 1 below.

TABLE 1

| Aging Period | Sensory Evaluation | | | | Aroma Component Isovaleric Acid Concentration |
| --- | --- | --- | --- | --- | --- |
| (day) | Taste | Texture | Flavor | Overall | (mg/g) |
| 5 | X | X | X | X | 0.44 |
| 10 | X | Δ | X | X | 0.49 |
| 15 | ◯ | ◯ | ◯ | ◯ | 0.70 |

TABLE 1-continued

| Aging Period | Sensory Evaluation | | | | Aroma Component Isovaleric Acid Concentration |
|---|---|---|---|---|---|
| (day) | Taste | Texture | Flavor | Overall | (mg/g) |
| 21 | ◯ | ◯ | ◯ | ◯ | 0.77 |
| 30 | ◯ | ◯ | ◯ | ◯ | 0.84 |

As shown in Table 1 above, it was confirmed that among the fermented foods produced under the conditions of this example, as a result of being aged for 15 days or more, the resulting fermented food has an increased isovaleric acid concentration and an excellent taste, texture, and flavor. Thus, in the example shown below, the aging period was set to 30 days.

Second Example

Next, cheese-like fermented foods of examples and comparative examples were produced by the method shown below, and the umami, flavor, and texture were evaluated in the same manner as in the first example.

As a soybean raw material, plain soymilk manufactured by Kikkoman Beverage Co., Ltd., heat-sterilized at a center temperature of 85° C. or more for 15 minutes was used. Lactic acid bacteria were added to the sterilized soybean raw material, and lactic acid fermentation was performed under the conditions shown in Table 2 below. The soybean soymilk obtained by this lactic acid fermentation was heat-sterilized at a center temperature of 85° C. or more for 1 minute, wrapped in a cotton cloth and a mold, and allowed to stand under pressure overnight to discharge whey, thereby forming a curd.

TABLE 2

| No. | Lactic Acid Bacteria | Fermentation Temperature (° C.) | Fermentation Time (hours) |
|---|---|---|---|
| 1 | Streptococcus thermophilus Lactobacillus delbrueckii subsp. bulgaricus Lactobacillus helveticus | 43 | 4.5 to 7 |
| 2 | Lactococcus lactis subsp. cremoris Lactococcus lactis subsp. lactis Leuconostoc mesenteroides subsp. cremoris Lactococcus lactis subsp. diacetylactis | 30 | 16 |
| 3 | Streptococcus thermophilus Lactobacillus delbrueckii subsp. bulgaricus Lactobacillus helveticus | 43 | 4.5 to 7 |
| 4 | Streptococcus thermophilus Lactobacillus delbrueckii subsp. bulgaricus Lactobacillus helveticus | 43 | 4.5 to 7 |

Next, the formed curd was broken once, and salt in amount of 4 mass % based on the total mass of the curd was added. The curd was then wrapped in a cotton cloth and a mold and allowed to stand under pressure for 5 hours, thereby reshaping the curd. Then, for the samples Nos. 1 to 3, spores of koji mold of each Koji mold shown in Table 3 below was sprayed to the entire surface of the obtained curd. At this time, a suspension of 0.103 g of spores of koji mold in 10 ml of a 0.9 mass % saline solution was used. Incidentally, no Koji mold was attached to the sample No. 4.

TABLE 3

| No. | Koji Mold | Aging Temperature (° C.) | Aging Period (day) |
|---|---|---|---|
| 1 | Aspergillus oryzae (Yoi Tane Koji for Shoyu, manufactured by Bio'c Co., Ltd.) | 15 | 30 |
| 2 | Aspergillus oryzae (Yoi Tane Koji for Shoyu, manufactured by Bio'c Co., Ltd.) | 15 | 30 |
| 3 | Aspergillus sojae + Aspergillus oryzae (Yoi Tane Koji Sojae, manufactured by Bio'c Co., Ltd. ) | 15 | 30 |
| 4 | None | 15 | 30 |

The Koji mold-attached curd was allowed to stand under a temperature condition of 25° C. for 2 or 3 days to grow the Koji mold until the surface became yellow and slightly green. Then, each sample was placed in a film bag containing an oxygen scavenger, hermetically sealed, and allowed to stand under a temperature condition of 15° C. for 30 days to be aged. The results of the above are shown in Table 4 below.

TABLE 4

| No. | Taste | Texture | Flavor | Overall |
|---|---|---|---|---|
| 1 | ◯ | ◯ | ◯ | ◯ |
| 2 | ◯ | ◯ | ◯ | ◯ |
| 3 | ◯ | ◯ | ◯ | ◯ |
| 4 | X | X | X | X |

As shown in Table 4 above, the samples Nos. 1 to 3 produced by the production method of the present invention were excellent in all of taste, texture, and flavor. Meanwhile, sample No. 4, which was not fermented or aged with a Koji mold, did not have a cheese-like flavor and was not smooth either.

Third Example

In this example, cheese-like fermented foods were prepared changing the blending ratio between soymilk and okara, and the flavor and texture were evaluated.
<Sample Preparation>

As the raw material of the example, a raw material in which a predetermined amount of soymilk okara (soymilk okara powder, manufactured by Kikkoman Soyfoods Co., Ltd.) was added to soymilk (plain soymilk manufactured by Kikkoman Beverage Co., Ltd.) was used. Then, water was added to the raw material if necessary, and heat sterilization was performed at a center temperature of 85° C. or more for 15 minutes. Lactic acid bacteria (Streptococcus thermophilus, Lactobacillus delbrueckii subsp. bulgaricus, and Lactobacillus helveticus) were added thereto, followed by fermentation at 43° C. for 7 hours.

The obtained lactic acid fermented product (coagulated product) was heat-sterilized at a center temperature of 85° C. or more for 1 minute, then wrapped in a cotton cloth and a mold, and allowed to stand under pressure overnight to discharge whey, thereby forming a curd. Subsequently, the formed curd was broken once, and salt in amount of 4 mass % based on the total mass of the curd was added. The curd was then wrapped in a cotton cloth and a mold and allowed to stand under pressure for 5 hours, thereby reshaping the curd.

Next, to the entire surface of the obtained curd, a suspension of 0.103 g of spores of koji mold of Aspergillus oryzae (Yoi Tane Koji for Shoyu, manufactured by Bio'c Co., Ltd.)

in 10 ml of a 0.9 mass % saline solution was sprayed. The Koji mold-attached curd was allowed to stand under a temperature condition of 25° C. for 2 or 3 days to grow the Koji mold until the surface became yellow and slightly green. Further, each sample was placed in a film bag containing an oxygen scavenger, hermetically sealed, and allowed to stand under a temperature condition of 15° C. for 4 to 8 weeks to be aged.

<Evaluation>

After aging for a predetermined period, each sample was taken out from the bag and subjected to sensory evaluation by two panelists for texture (smoothness) and flavor (cheese-like flavor). With respect to "flavor", ○ was given when the two panelists both noted a flavor similar to cheese, Δ was given when one of them noted a flavor similar to cheese, and × was given when none of them noted a flavor similar to cheese. With respect to "texture", ○ was given when the two panelists both noted smoothness (no roughness), Δ was given when only one of them noted smoothness, and × was given when they both noted roughness.

The results of the above are shown in Table 5 below. Incidentally, the remainder of the raw material composition shown in Table 5 below includes moisture and the like contained in soymilk okara.

flavor (cheese-like flavor), and texture (smoothness) were evaluated. The aroma component was also analyzed.

<Evaluation>

For "flavor" and "texture", sensory evaluation was performed in the same manner under the same conditions as in the first embodiment. In addition, sensory evaluation for "taste" was also performed by two panelists. ○ was given when two panelists both noted umami, Δ was given when one of them noted umami, and × was given when none of them noted umami.

The aroma component was analyzed by gas chromatography (HERACLES II, manufactured by Alpha Moss Japan), and the concentration of isovaleric acid, which is the aroma component peculiar to cheese, was calculated. At this time, 2 g of a sample was enclosed in a 20-ml vial, and the components inside the vial were concentrated and extracted by SPME (solid-phase microextraction method). The trap temperature was set at 40° C./240° C. (desorption temperature), and hydrogen was used as the carrier gas. A metal capillary column (MXT-5/MXT-WAX) was used as the column, and the column temperature rise conditions were such that the initial temperature was 40° C., the initial isothermal time was 10 seconds, and the temperature was

TABLE 5

| | Formulation (g) | | | | | | | |
| | Raw Material Composition | | | | Evaluation Results | | | |
| | Soymilk | | | | | | Texture | |
| | Okara (dry mass) | Soymilk | Remainder | Water | Flavor | 4 weeks | 6 weeks | 8 weeks |
|---|---|---|---|---|---|---|---|---|
| Reference Example | 0 | 870 | 0 | 0 | ○ | ○ | ○ | ○ |
| Example A1 | 27.9 | 570 | 2.1 | 0 | ○ | ○ | ○ | ○ |
| Example A2 | 37.2 | 470 | 2.8 | 50 | ○ | ○ | ○ | ○ |
| Example A3 | 55.8 | 270 | 4.2 | 330 | ○ | X | ○ | ○ |
| Example A4 | 65.1 | 170 | 4.9 | 530 | ○ | X | Δ | Δ |
| Comparative Example B1 | 74.4 | 70 | 5.6 | 650 | ○ | X | X | X |
| Comparative Example B2 | 80.9 | 0 | 6.1 | 783 | ○ | X | X | X |

As shown in Table 5 above, the fermented food of Comparative Example B1, in which the blending amount (dry mass) of okara was more than 50 mass % of the total mass of the raw material, and the fermented food of Comparative Example B2, which was produced from okara and water without using soymilk, had a flavor similar to cheese, but roughness remained even after aging, resulting in an inferior texture. In contrast, the fermented foods of Examples A1 to A4, which were produced from a raw material in which okara was blended with soymilk such that the okara content (dry mass) was 50 mass % or less of the total mass, did not have the grassy smell peculiar to soybeans, had a flavor similar to cheese, and offered a smooth texture.

Fourth Example

Next, fermented foods were produced in the same manner as for the fermented food of Example A2 described above changing only the aging period, and the taste (umami), raised from 40° C. to 250° C. at a temperature rise rate of 1.5° C./sec. Detection was performed at an FID temperature of 260° C.

The results of the above are shown in Table 6 below.

TABLE 6

| Aging Period | Sensory Evaluation | | | | Aroma Component Isovaleric Acid Concentration |
| (day) | Taste | Texture | Flavor | Overall | (mg/g) |
|---|---|---|---|---|---|
| 0 | X | X | X | X | 0.25 |
| 10 | Δ | X | X | X | 0.62 |
| 20 | ○ | ○ | ○ | ○ | 0.65 |
| 30 | ○ | ○ | ○ | ○ | 1.01 |

As shown in Table 6 above, the fermented foods containing 0.65 mg/g or more of isovaleric acid were excellent in all of taste (umami), texture, and flavor.

From the above results, it was confirmed that according to the present invention, a cheese-like fermented food that has a flavor and texture similar to cheese can be produced from a soybean raw material. In particular, it was confirmed that use of a raw material containing soymilk and okara makes it possible to produce a cheese-like fermented food that has a flavor and texture similar to cheese and allows for easy ingestion of dietary fiber that we tend to be deficient in.

The invention claimed is:

1. A method for manufacturing a cheese-like fermented food, comprising:

a coagulation step of coagulating a soybean raw material using at least one member selected from lactic acid bacteria, acids, and coagulants;

a step of separating whey from a coagulated product obtained in the coagulation step, thereby forming a curd; and a step of fermenting and aging the curd by a Koji mold, wherein in the fermentation and aging step, a liquid containing spores of koji mold is sprayed to a surface of the curd.

2. The method for manufacturing a cheese-like fermented food according to claim 1, wherein the soybean raw material contains soymilk manufactured using dehulled soybeans.

3. The method for manufacturing a cheese-like fermented food according to claim 1, wherein the soybean raw material contains soymilk and okara, and a dry mass of the okara is 50 mass % or less (excluding 0 mass %) of a total mass.

4. The method for manufacturing a cheese-like fermented food according to claim 3, wherein a blend of 2.5 to 38.3 parts by mass, on a dry mass basis, of okara with 100 parts by mass of soymilk is used as the soybean raw material.

5. The method for manufacturing a cheese-like fermented food according to claim 3, wherein one or both of the soymilk and the okara is manufactured using dehulled soybeans.

6. The method for manufacturing a cheese-like fermented food according to claim 3, wherein an okara powder having a particle size of 500 μm or less is used as the okara.

7. The method for manufacturing a cheese-like fermented food according to claim 1, wherein in the fermentation and aging step, a Koji mold variety used for soy sauce production and/or a Koji mold variety used for miso production is used as the Koji mold.

8. The method for manufacturing a cheese-like fermented food according to claim 1, wherein the Koji mold is *Aspergillus oryzae* and/or *Aspergillus sojae*.

9. The method for manufacturing a cheese-like fermented food according to claim 4, wherein one or both of the soymilk and the okara is manufactured using dehulled soybeans.

10. The method for manufacturing a cheese-like fermented food according to claim 4, wherein an okara powder having a particle size of 500 μm or less is used as the okara.

11. The method for manufacturing a cheese-like fermented food according to claim 3, wherein the Koji mold is *Aspergillus oryzae* and/or *Aspergillus sojae*.

12. The method for manufacturing a cheese-like fermented food according to claim 3, wherein in the fermentation and aging step, a liquid containing spores of Koji is sprayed to a surface of the curd.

13. The method for manufacturing a cheese-like fermented food according to claim 3, wherein in the fermentation and aging step, spores of Koji, soybean Koji, or rice Koji is mixed with the curd.

14. A method for manufacturing a cheese-like fermented food, comprising:

a coagulation step of coagulating a soybean raw material using at least one member selected from lactic acid bacteria, acids, and coagulants;

a step of separating whey from a coagulated product obtained in the coagulation step, thereby forming a curd; and a step of fermenting and aging the curd by a Koji mold, wherein in the fermentation and aging step, spores of koji mold, soybean Koji, or rice Koji is mixed with the curd.

15. The method for manufacturing a cheese-like fermented food according to claim 14, wherein the soybean raw material contains soymilk manufactured using dehulled soybeans.

16. The method for manufacturing a cheese-like fermented food according to claim 14, wherein the soybean raw material contains soymilk and okara, and a dry mass of the okara is 50 mass % or less (excluding 0 mass %) of a total mass.

17. The method for manufacturing a cheese-like fermented food according to claim 16, wherein a blend of 2.5 to 38.3 parts by mass, on a dry mass basis, of okara with 100 parts by mass of soymilk is used as the soybean raw material.

18. The method for manufacturing a cheese-like fermented food according to claim 16, wherein one or both of the soymilk and the okara is manufactured using dehulled soybeans.

19. The method for manufacturing a cheese-like fermented food according to claim 16, wherein an okara powder having a particle size of 500 μm or less is used as the okara.

20. The method for manufacturing a cheese-like fermented food according to claim 14, wherein in the fermentation and aging step, a Koji mold variety used for soy sauce production and/or a Koji mold variety used for miso production is used as the Koji mold.

* * * * *